United States Patent [19]

Lai et al.

[11] Patent Number: 4,780,495

[45] Date of Patent: Oct. 25, 1988

[54] N-(SUBSTITUTED)-α-(3,5-DIALKYL-4-HYDROXYPHENYL)-α,α-DISUBSTITUTED ACETAMIDES, AND COMPOSITION STABILIZED THEREWITH

[75] Inventors: John T. Lai, Broadview Heights; Pyong N. Son, Akron, both of Ohio

[73] Assignee: The B. F. Goodrich Company, Akron, Ohio

[21] Appl. No.: 147,836

[22] Filed: Jan. 25, 1988

Related U.S. Application Data

[63] Continuation-in-part of Ser. No. 887,458, Jul. 21, 1986, abandoned, which is a continuation-in-part of Ser. No. 549,036, Nov. 7, 1983, abandoned.

[51] Int. Cl.[4] .................... C07D 241/04; C08K 5/34
[52] U.S. Cl. ............................ 524/100; 44/63; 252/51.5 A; 544/231; 544/382; 544/384; 544/386; 544/389; 544/400; 544/397; 544/393
[58] Field of Search ............ 544/231, 382, 386, 389, 544/391, 393, 397, 400; 524/100; 44/63; 252/51.5 A

[56] References Cited

U.S. PATENT DOCUMENTS

| | | | |
|---|---|---|---|
| 4,292,409 | 9/1981 | Lai et al. | 544/384 |
| 4,547,538 | 10/1985 | Lai et al. | 524/100 |
| 4,650,870 | 3/1987 | Conetta et al. | 524/100 |

OTHER PUBLICATIONS

Testa, et al., "Chemical Abstracts", vol. 65, 1966, col. 20083g.

Primary Examiner—Richard L. Raymond
Assistant Examiner—James H. Turnipseed
Attorney, Agent, or Firm—Alfred D. Lobo; Nestor W. Shust

[57] ABSTRACT

N-(substituted)-1-(piperazinealkyl)-α-(3,5-dialkyl-4-hydroxyphenyl)-α,α-disubstited acetamides, are novel compounds prepared by a novel modification of the ketoform process. The compounds are useful as stabilizers for organic materials subject to degradation in an environment in which the materials are exposed to heat, oxidation and light, particularly ultraviolet light. The compounds are especially useful in combination with known secondary stabilizers.

13 Claims, No Drawings

N-(SUBSTITUTED)-α-(3,5-DIALKYL-4-HYDROXY-PHENYL)-α,α-DISUBSTITUTED ACETAMIDES, AND COMPOSITION STABILIZED THEREWITH

CROSS-REFERENCE TO RELATED APPLICATIONS

This application is a continuation-in-part of Ser. No. 887,458 filed July 21, 1986, now abandoned which in turn is a continuation-in-part of application Ser. No. 549,036 filed Nov. 7, 1983, now abandoned.

BACKGROUND OF THE INVENTION

The novel compounds of this invention are N-(substituted)α-(3,5-dialkyl-4-hydroxyphenyl)-α,α-disubstituted acetamides in which one of the substituents on the N atom is a polysubstituted piperazine, or, a 2-piperazinone group. More correctly, the compounds are "N-(substituted)-1-(piperazinealkyl)-α-(3,5-dialkyl-4-hydroxyphenyl)-α,α-substituted acetamides", and "N-(substituted)-1-(piperazin-2-onealkyl)-α-(3,5-dialkyl-4-hydroxyphenyl)-α,α-substituted acetamides", either or both of which are hereinafter referred to as "3,5-DHPZNA" for brevity. These compounds have never heretofore been made because the tertiary alpha-carbon ("alpha-C") atom (alpha relative to the phenyl ring) of any reactant from which such a compound might have been derived, is so hindered that it does not permit reaction with an amine to form the amide which, conventionally, one might expect to be formed. By "tertiary" C atom we refer to a C atom bonded only to C atoms. The distinctive feature of our compounds is that they are acetamides in which the tertiary C atom, referred to as "the alpha C atom" because it is alpha to the hydroxyphenyl ring, and also alpha to the carbonyl C atom, is disubstituted. In other words, there is only a single, disubstituted C atom, connecting the hydroxyphenyl ring to the carbonyl C atom of the disubstituted acetamide.

3,5-dialkyl-4-hydroxyphenyl organic compounds, referred to as "hindered phenols" because of the substituents on the ring C atoms flanking the ring C atom carrying the hydroxyl (OH) group, have been of great interest for some time because of their stabilization activity. This interest derived from the discovery that such compounds were excellent antioxidants, this property in turn, being related to the stability of the aroxyl radical represented by the typical structure

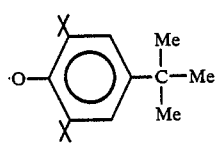

Me=methyl wherein the "cross" substituents represent t-butyl, written out in greater detail on the 1-C atom. It was, until the discovery of the 3,5-DHPZNA radical, one of the most stable aroxyl radicals known. This prior art aroxyl radical was referred to as the "blue aroxyl" in a lecture titled "The Blue Aroxyl, The First Stable Oxygen Radical, Its Discovery and Its Properties" given by Eugen Muller, in Lisbon on the 28th of May 1973 and printed in Rev. Port. Quim. 14, 129 (1972). The radical was referred to as "blue" because of the distinctive dark blue crystals obtained by shaking the benzene solution of 2,4,6-tri-tert.-butylphenol with potassium ferricyanide in aqueous alkali.

Since the effectiveness of hindered phenols to stabilize an organic material, subject to degradation due to heat, oxygen and light, appeared to be correlated to the stability of the aroxyl radical generated by exposure of the organic material, it seemed likely that modifications in the structure of such hindered phenols, particularly those modifications relating to the substituents on the 1-C atom of the phenyl ring, might provide aroxyl radicals which were more stable than those of the prior art. The quest appeared to devolve upon finding which particular substituent on the 1-C atom provided better stability of the radical than another substituent.

This general approach seemed to have been taken by prior workers in the field, for example by Meier et al in U.S. Pat. No. 3,247,240, though at the time, it can be assumed they were unaware of the existence of the aroxyl radical. Because he reacted 2,6-di-tert-butyl phenol with an alpha,beta-monoolefinically unsaturated compound such as methyl acrylate, he could never have substituted more than a single substituent on the alpha-C atom, that is, the alpha-C atom could never be a tertiary (that is, fully substituted) C atom. And, of course he could not have provided a substituted acetamide.

U.S. Pat. No. 3,338,833 to Spivack et al, issued soon thereafter, pursued the lead of Meier et al, but with substituted dialkyl-4-hydroxyphenyl amides having an alkylene ('spacer') group spacing the amide C atom from the phenyl ring. Again, the alpha-C atom could never have more than a single substituent on the alpha-C atom, that is, the alpha-C atom could never be a tertiary C atom. In the reaction schemes he suggests, he specifies the reactant hydroxyphenyl ester or acid chloride as having a $(CH_2)_n$ spacer where n is a small whole number, e.g. 1 or 2. Assuming one decided to impute and extend the enablement embodied in the Spivack '833 teachings to a spacer having a tertiary C atom, and, chose to make a hydroxyphenyl amide spaced from the phenyl ring only by the tertiary C atom, one would need to have access to the precursor hydroxyphenyl acid having the structure

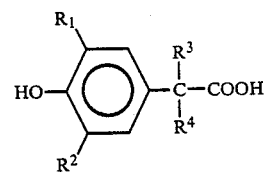

or its acyl derivative, wherein $R^1$ and $R^2$ represent alkyl, cycloalkyl, phenyl, alkyl-phenyl, naphthyl and alakylnaphthyl which serve to hinder the OH group, and $R^3$ and $R^4$ represent alkyl substituents, which acid or acyl derivative could then be used to react with an appropriate amine. This 3,5-dialkyl-4-hydroxyphenyl substituted acetic acid, to be used as a precursor is obtained as disclosed in my U.S. Pat. No. 4,523,032 and is not a prior art compound. The corresponding ester, however, is a prior art compound and may be obtained as disclosed in 3,455,994 to Knell. I therefore reacted the ester, namely methyl α-(3,5-di-t-butyl-4-hydroxyphenyl)-α-methylpropionate, which is a prior art compound, with tert-octylamine at 150°–160° C. for 4 hr but failed to find any trace of the expected amide with the tertiary alpha C atom. I then continued the reaction at 160°–170° C. for an additional 2 hr and still failed to obtain the expected product.

To make certain this lack of reactivity was not due at least in part to the steric hindrance of the amine group of the tert-octylamine, I chose to minimize any such effect by substituting a long straight chain alkylamine, namely octadecylamine, for the t-octylamine. I then conducted a reaction with octadecylamine and methyl α-(3,5-di-t-butyl-4-hydroxyphenyl)-α-methylbutyrate in an analogous manner and under the same conditions of reaction as those described immediately hereinabove. I found the octadecylamine failed to react with the methyl α-(3,5-di-tert.butyl-4-hydroxyphenyl)-α-methylbutyrate. Only a trace of high mol wt material was detected by mass spectrography. This trace of material was identified as the dimer of the amine having a mol wt of 520. The remaining material consisted of the unrected reactants. No amide with a tertiary alpha-C atom was obtained.

Later, in U.S. Pat. No. 3,787,355, Linhart et al, like Spivack '833, chose an alkylene spacer, but changed the amine believing this might provide more effective stabilization. Like Linhart et al, Spivack also pursued the 'bulking of the molecule' as a path to more effective stabilization in U.S. Pat. No. 4,049,713, but retained the alkylene spacer between the ester group, or amide group, and the phenyl ring in his hindered hydroxyphenyl alkanoates and amides. Since he had started with a compound which had either only one substituent on the alpha-C atom, or none, the esters he made were prepared via usual esterification procedures from a suitable alcohol and a carboxylic acid derivative of the substituted hindered phenol of interest, it is clear he could never have made an ester with a tertiary alpha-C atom.

In U.S. Pat. No. 4,191,683, Brunetti et al decided upon a polysubstituted piperidyl alkylamine, or a dimer or trimer of it, without linking their compounds to a hydroxyphenyl moiety, clearly indicating that at that time, there was no suggestion that an aroxyl radical might advantageously be combined with a polysubstituted piperidyl alkylamine, irrespective of what linkage might be used. At least with respect to their dimer and trimer, the emphasis was on bulking the molecule.

It is evident that the opportunity to investigate the stability of an aroxyl radical having a disubstituted alpha-C atom did not present itself because the alpha C atom could not be disubstituted. This inability is borne out by the efforts of Rosenberger et al in U.S. Pat. No. 4,197,236, who were able to produce an alkyl (methyl) substituent on a tertiary C atom (see example 3) but were forced to provide an alkylene spacer between the tertiary C atom and the carbonyl C atom, to obviate the steric hindrance and allow the reaction to proceed. When they coupled the alpha C atom to the carbonyl C atom of the carboxyl group (see example 1), the alpha C was not disubstituted. However, their pursuit of a "bulked-up" acetamide molecule was successful. They were able to provide two hydroxyphenyl groups on the tertiary C atom with the expectation of providing a more stable diradical. This was a different approach towards the same goal we pursued, namely finding and synthesizing a more effective stabilizer. They opted to cope with the destabilizing effect of the tendency of each of the two radicals connected to the single C atom, to form a quinone methide, but benefitted from the bulked up molecule. We chose to use a single hydroxyphenyl radical in which the stability was enhanced by the lone disubstituted alpha C atom connecting the hydroxyphenyl ring to the carbonyl C atom. Because the generation of an aroxyl radical with enhanced stability is the nexus of the activity of our compounds it is evident that they are distinct and different from the dihydroxyphenyl piperidyl compounds of the '236 patent.

Not long afterwards, in U.S. Pat. No. 4,246,198, Rosenberger et al pursued the notion of bulking the molecule even further by forming a dimer or trimer after bulking the substituent on the 1-C atom of the phenyl ring. In each embodiment he provided an alkylene spacer ($C_xH_{2x}$) in which x is defined as being 0, 1, 2 or 3, optionally in combination with another such alkylene spacer ($C_yH_{2y}$). But the disclosure of the value "0" for x was clearly accidental since there is no suggestion provided to enable one to make such a compound. Nor is there any suggestion that such a compound, which they were earlier unable to make, might now have been made by them in this '198 patent. From the numerous examples given in the specification, it is clear that they did not make such a compound. This is confirmed by their statement that in the preferred compounds they made, x an y are each either 1 or 2. From the foregoing evidence of insurmountable difficulty I encountered in my attempts to produce such a compound by any known synthesis other than the ketoform synthesis, it is clear that those known syntheses could not have been used to make such a compound. Further, it is clear that the amine group in any of their compounds is an amine linkage which must always be a secondary amine —NH—; and the H in this linkage cannot be substituted.

Much later, in U.S. Pat. No. 4,452,884, Leppard disclosed combining a hydroxyphenyl group in which the 3,5-dialkyl substituents would produce a stable aroxyl radical, except that, having recognized that "A" in his structure could not be a disubstituted lone C atom (the alpha C atom), he specified that A is methylene or one of several groups having plural C atoms connecting the hydroxyphenyl group to the carbonyl C atom in his structure. In a subsequent patent (U.S. Pat. No. 4,518,679) Leppard et al disclosed many other piperidinyl derivatives linked to hydroxyphenyl groups with various linkages, none of which has the disubstituted alpha C atom connecting the phenyl ring to an amide carbonyl C atom. Thus it is evident that our 3,5-DHPZNA compounds are distinct and different from the hydroxyphenyl piperidyl compounds of both the '884 and the '679 Leppard patents.

It was in the foregoing framework of related aroxyl radicals with varying degrees of stability, measured as described hereinbelow, that I joined the search for a more stable aroxyl radical than the blue aroxyl radical, and sought to introduce the radical into a compound which might have enhanced stabilization activity.

Though I subscribed to the general notion that some bulking of the 1-C substituent would likely produce enhancement of the stability of the bulked up aroxyl radical, relative to that of the blue aroxyl radical, there was no clear indication as to what might constitute the 'proper' bulking. Many bulked up aroxyl radicals are less stable than the blue aroxyl, but there was no way of linking their activity to the lack of a disubstituted alpha-C atom. The disubstituted alpha-C atom was only present on the blue aroxyl radical in which the 3- and 5-carbons also had substituents which contained a disubstituted C-atom, and there was no particular reason to ascribe greater significance to the presence of such a C-atom in the substituent on the 1-C atom. Nor was there any reason to believe that an amide substituent might be about 50 times more effective than the blue aroxyl radical, and far more effective than other prior art 'bulking' substituents, if it could be made to include a disubstituted alpha-C atom. The optional presence of an alkylidene group between the carbonyl C atom and the N atom of the carboxyamide is incidental to producing desirable "bulking" by chain extension, and has no known theoretical relevance with respect to influencing the reactivity of the alpha C atom, and is not found to have any.

Apart from the inability to produce a disubstituted alpha C atom with a monohydroxyphenyl group in the structure, it is worth noting that, in prior art hindered phenol hydroxyphenylalkyleneyl isocyanurates which are antioxidants having superior effectiveness, for example, Irganox 1010, there are at least two C atoms in the linkage connecting the 1-C atom of the hydroxyphenyl ring to the rest of the molecule. It is this structure which in no small measure accounts for their effectiveness. As will be evident from data presented hereinafter, the compounds of our invention are inferior antioxidants, this property being attributable to the disubstituted alpha C atom; but they have a surprisingly superior stabilizing effect against degradation by ultraviolet light, attributable to the stability of the aroxyl radical formed.

Despite the activity of the 3,5-DHPZNA stabilizers of this invention, they would be of little value if they could not be made in good yields, that is, at least 50%. I found that a good yield of 3,5-DHPZNA was not obtained without one of the 3- or 5-alkyl substituents on the 3,5-DHPZNA being a tertiary alkyl substituent, which dictates one substituent on the 2,6-dialkyl phenol starting material. It is much preferred to have tert.-alkyl substituents on each of the 2- and 6-carbon atoms.

SUMMARY OF THE INVENTION

It has been discovered that a N-(substituted)-1-(piperazinealkyl)-$\alpha$-(3,5-dialkyl-4-hydroxyphenyl)-$\alpha,\alpha$-disubstituted acetamide, or, a N-(substituted)-1-(piperazin-2-one-alkyl)-$\alpha$-(3,5-dialkyl-4-hydroxyphenyl)-$\alpha,\alpha$-disubstituted acetamide, either of which is referred to as "3,5-DHPZNA" herein, for brevity, generates an exceptionally stable hindered acetamide-aroxyl radical which is far more stable than the "blue aroxyl radical" derived from 2,4,6-tri-t-butylphenol, which radical was heretofore adjudged the standard of superior stability and resistance to degradation due to heat, oxygen and light, the compound having been specifically disclosed as a uv-stabilizer.

It is therefore a general object of this invention to provide a class of hindered phenols which are disubstituted acetamides which generate substituted aroxyl radicals far more stable than known aroxyl radicals. The substituents on the alpha-C atom of the precursor provide such great steric hindrance that, when such substituents are present on a 4-hydroxy phenyl ester, used as a precursor for the formation of the desired hindered acetamide by reaction with an appropriately substituted amine, the reaction is negated.

It has also been discovered that a hindered aroxyl amide radical which is at least ten times more stable than the "blue aroxyl radical" heretofore deemed stable, may be generated by 3,5-DHPZNA compounds prepared by a peculiarly effective synthesis known as the ketoform reaction. This ketoform reaction is unexpectedly well-adapted to produce the 3,5-DHPZNA compounds which we have been unable to produce by any other synthesis known to us.

It is therefore a general object of this invention to provide an elegant, yet simple synthesis for the commercial production of 3,5-DHPZNA compounds which are useful as antioxidants and light stabilizers, particularly under elevated temperature conditions to which organic materials are subject in the environments in which they are used. The process comprises reacting a 2,6-dialkylphenol, a chloroform or bromoform, and an appropriately substituted aminopolysubstituted piperazine, or, substituted aminopolysubstituted piperazin-2-one, in the presence of an alkali metal hydroxide to form the desired 3,5-DHPZNA.

It is a specific object of this invention to provide a 3,5-DHPZNA which generates a hindered carboxyamide aroxyl radical which is so stable that a very small amount of the hindered aroxyl acetamide radical, derived from a compound of this invention which compound is present in the range from about 0.01 to about 1 phr (part per hundred parts organic material to be stabilized), provides satisfactory stability of the material containing the compound.

DETAILED DESCRIPTION OF PREFERRED EMBODIMENTS

This search for a more stable aroxyl radical was spurred by the notion that the steric configuration of the alpha-C atom connecting the 1-C atom of the phenyl ring and the carbonyl C atom, peculiarly enhanced the stability of an aroxyl radical. In due course, this search led to amides, and more specifically substituted acetamides, which we hoped, might further enhance the stability of the aroxyl radical. Except, as stated hereinbefore, there was no known way of overcoming the steric hindrance which frustrated the formation of the 3,5-DHPZNA we desired to make and test.

It was only because of the earlier discovery of the ketoform reaction (U.S. Pat. No. 4,466,915 to John T. Lai) for the preparation of a 2-keto-1,4-diazacycloalkane, that we resorted to the use of a ketone and an amine in the presence of a haloform and alkali in a synthesis for the 3,5-DHPZNA. We were happily surprised to find that, despite the lack of similarity between the formation (by cyclization) of a 2-keto-1,4-diazacycloalkane, and the attack of a 1-C atom of a phenyl ring, the combination of an appropriate ketone and amine in the presence of chloroform or bromoform and an alkali, successfully introduced a subsituent with a tertiary alpha-C atom on the 1-C atom of the phenyl ring, and generated the substituted acetamide.

Though all hindered phenols (referring to the hindrance of the OH group) have a stabilizing effect, the search for a more effective aroxyl radical requires testing of the radicals derived from a wide option of substituents on the 1-carbon atom of the phenyl ring. Such testing is done by measuring the half-life of each radical. The half life ("t $\frac{1}{2}$") is the time it takes for the aroxyl radical to lose 50% of its intensity, as evidenced by the height of the peak registered in an Electron Spin Resonance (ESR) Spectroscope. To make the measurement, 50 ml toluene with potassium ferricyanide and aqueous alkali are placed in a 250 ml three-necked flask equipped with a magnetic stirrer. The solution turns orange. The hindered phenol being tested is dissolved, in 50 ml toluene, and the solution added, a little at a time over about 45 min, to the flask. The solution turns blue-green and is stirred under nitrogen for 2 hr. A 10 ml sample is withdrawn and diluted to 100 ml with toluene to provide a $10^{-3}$ molar concentration. It is dried by adding $Mg_2(SO_4)_2$, then filtered. The filtrate in a tube is then placed in the ESR 'scope and an initial reading is made. Then, after preselected intervals, usually 0.5 hr, the peak height of the sample is again measured, and the procedure repeated until a peak one-half the height of the original peak is registered. The combined intervals of time after which this last measurement was made is defined as the half-life of the radical. A precise half-life is obtained by plotting peak height vs. time.

Representative prior art compounds were prepared and tested following the foregoing procedures. Such compounds were chosen because of (i) the specific nature of substitution on the alpha-C atom, and (ii) the "bulking effect" provided by an unsubstituted, or, a single substituent on the alpha-C atom in the acetamide, or, by a "spacer" as in β-(3,5-di-t-butyl-4-hydroxyphenyl)-propanamide.

The criticality of the substituents on the alpha-C atom of the acetamide is best demonstrated by comparing three 3,5-DPHA compounds differing only in the linkage connecting the hydroxyphenyl ring to the carbonyl C atom.

In the prior art compounds herebelow, as in the substituted acetamides of this invention, no distinction is made between the effect of substituents on the N atoms, to the extent that each N atom is tertiary and di-alkyl-substituted, except that (i) compound A, disclosed in Spivack '833 has only a single methyl substituent on the alpha-C atom; (ii) compound B disclosed in Spivack '713 has no substituent on the alpha-C atom; and (iii) compound C disclosed in Linhart '355 has an unsubstituted alpha-C atom, but the extra C atom is in the dimethylene spacer connecting the hydroxyphenyl ring to the carbonyl C atom. This compound C differs from those disclosed in U.S. Pat. No. Re. 27,004 to Meier, in that the alpha-C atom in the latter may have a single substituent.

The results for the stability of the aroxyl radicals listed herebelow (the crosses represent t-butyl substituents) are derived from such prior art compounds by oxidation with potassium ferricyanide in aqueous alkali.

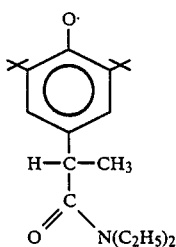

Compound A

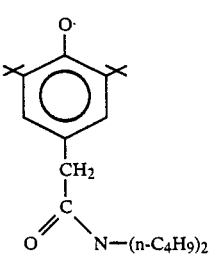

Compound B

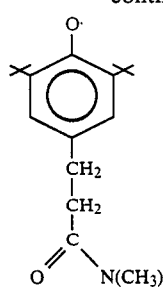

Compound C

Half life "t ½" of each of the above is less than 0.5 hr.

Each of the foregoing prior art radicals is less stable than the blue aroxyl radical which has a half-life of 0.5 hr, deemed very good.

By comparison with prior art aroxyl radicals, those derived from 3,5-DHPZNA compounds of this invention are many times more stable, as evidenced by the following measurement of the stability of a particular 3,5-DHPZNA aroxyl radical by the procedure described hereinabove. The particular compound (prepared as in example 1) tested has methyl substituents on the alpha-C atom, and the 1,4-diaza ring is a polysubstituted 2-keto-piperazinone.

| Compound 1 (made in example 1 herebelow) | Half-life |
| --- | --- |
| N—isopropyl-N—[2-(2-keto-3,3,5,5-tetramethyl-1-piperazinyl)ethyl]-2-(3,5-di-t-butyl-4-hydroxyphenyl)-2-methyl propanamide | >30 hr |

From the foregoing result it is evident that the aroxyl radical derived from the dimethyl-substituted alpha-C atom of a specific compound of this invention is unexpectedly over sixty times more stable than prior art aroxyl radicals derived from prior art compounds which do not have a disubstituted alpha-C atom. It is not expected that the substituents on the N atom have comparable influence on the stability of the aroxyl radical because of their relatively greater distance.

Test samples are prepared by mixing a predetermined amount of stabilizer into PP in a Brabender Plasticorder fitted with a Cam-Head (mixing chamber). The PP is first masticated for 1.5 min at 190° C. The stabilizer is then added followed by 3 min additional mixing. The stabilized mass of PP is removed and pressed into 20 ml thick sheets from which 1"×1" plaques are cut for oven aging. Type C (3"×0.125" wide) tensile bars are cut for UV stability tests.

Thermal oxidative stability (oven aging) is measured by aging the samples in triplicate in an air-circulating oven at 125° C. The time to failure, indicated by crumbling of the sample when rubbed between the fingers of one hand, was recorded as number of days to failure. Each sample contained 0.1 phr (part of stabilizer per 100 parts of PP).

Samples containing 0.1 phr of stabilizer to be tested are also tested for uv-stability, i.e. resistance to degradation by ultraviolet light. The samples were tested in an Atlas Xenon Weatherometer, Model No. 65-WR, equipped with a 6500 watt Xenon burner tube in accordance with ASTM D 2565-79-A. The black panel temperature was 60° C. The samples were subjected to an 18-min water cycle every 2 hr. The time in hrs to a 50% loss in tensile strength was determined. For a control, and standard for comparison, a sample containing no stabilizer is also tested.

The comparative effectiveness of the stabilization to degradation, by uv-light, provided by compounds having (i) no substituent on the alpha-C atom, (ii) only one substituent on the alpha-C atom, and (iii) two substituents on the alpha-C atom, but keeping the substituents on the N atom the same, is demonstrated by incorporating each, at various levels of concentration, in PP, and testing as stated immediately hereinabove.

| | | phr | |
|---|---|---|---|
| Compound | 0.05 | 0.1 hours | 0.2 |
| 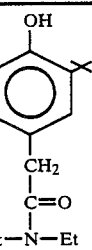 | 360 | 510 | 600 |
|  | 450 | 615 | 785 |
| 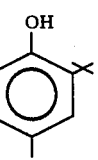 | 610 | 820 | 970 |

The effectiveness of the 3,5-DHPZNA compounds as stabilizers was tested in an analogous manner by incorporating them in polypropylene (PP) test samples, exposing the samples to a polymer-degrading level of heat and light, and recording the time after which a sample loses 50% of its tensile strength. The test results set forth hereafter are evidence that samples stabilized with a wide variety of substituents on the disubstituted alpha-C atom exhibit excellent stability to uv light.

The foregoing compound of example 1 of this invention is representative of a N-substituted-N-polysubstituted-1,4-diaza-2-(3,5-dialkyl-4-hydroxyphenyl)-2,2-substituted acetamide, represented by the structure

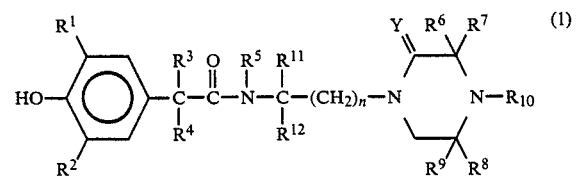

-continued
3,5-DHPZNA wherein
$R^1$, $R^2$ and $R^5$ each represent hydrogen, $C_1$-$C_{12}$ alkyl, phenyl, naphthyl, $C_1$-$C_8$, cycloalkyl, and, alkyl-substituted cycloalkyl, phenyl and naphthyl, each alkyl substituent being $C_1$14 $C_8$, and at least one of $R^1$ and $R^2$ is t-$C_4$-$C_{12}$ alkyl;

$R^3$ and $R^4$ independently represent $C_1$-$C_{18}$ alkyl, and $C_5$-$C_{12}$ cycloalkyl, phenyl and naphthyl, and, alkyl-substituted cycloalkyl, phenyl and naphthyl, each alkkyl substituent being $C_1$-$C_8$, and, when together cyclized, $R^3$ with $R^4$ may represent $C_4$-$C_{12}$ cycloalkyl, and $C_1$-$C_8$ alkyl-substituted cycloalkyl;

$R^6$, $R^7$, $R^8$ and $R^9$ each represent $C_1$-$C_{12}$ alkyl, or, when together cyclized, $R^6$ with $R^7$, and $R^8$ with $R^9$, may represent $C_4$-$C_{12}$ cycloalkyl, and $C_1$-$C_8$ alkyl-substituted cycloalkyl;

$R^{10}$ is selected from the group consisting of hydrogen, $C_1$-$C_8$ alkyl and

wherein
$R^{13}$ represent hydrogen, $C_1$-$C_{18}$ alkyl or alkenyl, phenyl or naphthyl;

$R^{11}$ and $R^{12}$ independently represent hydrogen and $C_1$-$C_{18}$ alkyl;

n is an integer in the range from 1 to about 8; and,

Y represents $H_2$ when the diaza ring is piperazinyl, and O when the diaza ring represents piperazine-2-one.

It will be appreciated that when $R_{10}$ is to be acyl, it is introduced by an acylation step after formation of the 3,5-DHPZNA in which there is no substituent on the $N^4$ atom of the diazacycloalkane ring.

The process for preparing the foregoing 3,5-DHPZNA compounds comprises reacting a 2,6-dialkylphenol with at least an equimolar quantities of an aliphatic, cycloaliphatic or alkaryl ketone and a 4-aminopolysubstituted piperazine or 4-amino-polysubstituted piperazin-2-one in the presence of an alkali metal hydroxide, preferably at a temperature in the range from about −10° C. to about 50° C.

The 2,6-dialkylphenol reactant is represented by the structure

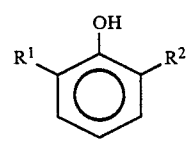

wherein $R^1$ and $R^2$ have the same connotations set forth hereinabove. Typical such reactants include 2-methyl-6-t-butylphenol, 2-ethyl-6-t-butylphenol, 2-propyl-6-t-butylphenol, 2-isopropyl-6-t-butylphenol, 2-n-butyl-6-t-butylphenol, 2,6-di-t-butylphenol, 2-n-amyl-6-t-butylphenol, 2-isoamyl-6-t-butylphenol, 2-heptyl-6-t-butylphenol, 2-isooctyl-6-t-butylphenol, 2-isopropyl-6-methylphenol, 2-n-butyl-6-isopropylphenol, 2-isopropyl-6-ethylphenol, 2-n-butyl-6-iosopropylphenol, 2-isoamyl-6-ethylphenol, 2-isoamyl-6-methylphenol, 2-isooctyl-6-methylphenol, 2-isooctyl-6-ethylphenol, 2-isooctyl-6-n-propylphenol, 2-isooctyl-6-n-hexylphenol, 2,6-di-(2-phenylpropyl)phenol, 2-methyl-6-(2-phenylpropyl)phenol, etc. the common being most preferred.

The 4-amino-polysubstituted piperazin-2-ones are N-substituted cyclic alkyleneimines represented by the structure

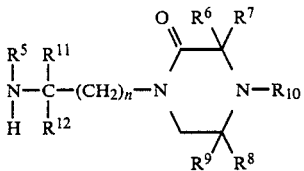

wherein $R^5$, $R^6$, $R^7$, $R^8$, $R^9$ and $R^{10}$ have the same connotation as that given hereinbefore. Two or more of the 4-amino-polysubstituted piperazinone moieties may be present on a single molecule, for example, when the moiety is a substituent in each of the two primary amine groups of an alkane diamine; or, of a triamine or tetramine. Preferred substituents are $C_1$-$C_8$ alkyl, branched or unbranched, and, preferred cyclic substituents are $C_3$-$C_6$ cycloalkyl in compounds exemplified by 4-methylamino-2,2,6,6-tetramethylpiperazin-2-one; 4-ethylamino-2,2,6,6-tetramethylpiperazin-2-one; 4-butylamino-2,2,6,6-tetramethyl-piperazin-2-one; N,N'-bis-(2,2,6,6-tetramethyl-4-piperazin-2-one)-1,6-hexanediamine, and the like.

Corresponding structurally analogous polysubstituted piperazines are represented by the structure

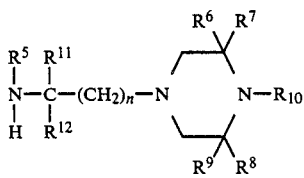

and are prepared from the foregoing piperazin-2-one by reduction, for example with lithium aluminum hydride (LiAlH$_4$) in refluxing tetrahydrofuran (THF). Typical polysubstituted piperazinesare 4-methylamino-2,2,6,6-tetramethylpiperazine; 4-ethylamino-2,2,6,6-tetramethylpiperazine; 4-butylamino-2,2,6,6-tetramethyl-piperazine; N,N'-bis(2,2,6,6-tetramethyl-4-piperazinyl)-1,6-hexanediamine, and the like.

The 3,5-DHPZNA is then produced by the ketoform reaction. As before, at least a stoichiometric amount of the 4-amino-polysubstituted piperazine is used, relative to the amount of 2,6-dialkylphenol, an excess of amine being preferred for good yields. Most preferred is up to a four-fold excess.

The ketone reactant may be a dialkylketone, a cycloalkanone, or alkylcycloalkanone, represented by the structure

(3)

wherein, $R^3$ and $R^4$ are independently selected from $C_1$-$C_8$ alkyl, preferably acetone, methyl ethyl ketone, methyl n-propyl ketone, diethyl ketone, 2-hexanone, 3-hexanone, di-n-propyl ketone, 2-octanone, methyl isopropyl ketone, and the like; or, when together cyclized, represent $C_5$-$C_{12}$ cycloalkyl, preferably cyclobutanone, cyclopentanone, cyclohexanone, cycloheptanone, cyclooctanone, cyclodecanone, methylcyclopentanone, methylcyclohexanone, dicyclohexyl ketone, and $C_1$-$C_4$ alkyl alkaryl ketones preferably acetophenone, o-methoxyacetophenone, p-chloroacetophenone, and the like.

It is preferred to use a stoichiometric excess of the ketone, sufficient to provide a solution for the organic reactants, but a greater than ten-fold excess serves no useful purpose. If a ketone solution is unnecesssary, less than a two-fold excess is generally found adequate.

Chloroform and bromoform may be interchangeably used, though the former, used in a slight, up to 50% molar excess relative to the 2.6-dialkyl phenol, is preferred. A larger excess greater than 1.5:1.0 simply interferes with work-up of the reaction mass.

The alkali metal hydroxide, typically sodium hydroxide or potassium hydroxide, is preferably used as a powder, or as a conc. aqueous solution, also in molar excess relative to the 2,6-dialkyl phenol, preferably from about a four- to eight-fold excess. Use of less than a four-fold excess will reduce the yield of product.

Although a catalyst may be used, it is not essential, and it is preferred not to use one. When used, preferred catalysts are the onium salts, that is, quarternary compounds of ions derived from Group VA and VIA elements, which compounds have the formula $(R'_4Y')^+X^-$ wherein $R'$ is a monovalent hydrocarbon radical including alkyl, aryl, alkaryl, cycloalkyl and like radicals, $Y'$ is phosphorus or nitrogen, and X is a halide, hydrogen sulfate, or like ions. Benzyltriethylammonium chloride (BTAC) has been found useful when used in an amount in the range from about 0.01 mole to about 0.1 mole of BTAC per mole of 2,6-dialkylphenol. Other catalysts useful in the process include tetraalkyl ammonium salts such as tetrabutyl ammonium bromide, tetrabutyl ammonium hydrogen sulfate, methyltrioctyl ammonium chloride, tetraalkyl phosphonium salts such as tetrabutyl phosphonium bromide, cetyltributyl phosphonium bromide, and the like.

A solvent for the organic reactants may be any polar organic solvent, and the ketone reactant itself may also function as the solvent. Commercially available solvents which are useful are methylene chloride, tetrahydrofuran, diethyl ether, dibutyl ether, dimethyl sulfone, 1,4-dioxane, carbon tetrachloride, toluene, and the like. The amount of solvent used is not critical, a 5 to 20-fold molar excess relative to the 2,6-dialkylphenol, and preferably a 7.5 to 15-fold excess, being generally used.

While the order of addition of the reactants is not narrowly critical, it is preferred that the alkali metal hydroxide be added last, and over a period of time, to control the reaction which is exothermic, and maintain the temperature below about 30° C., more preferably below about 10° C. The reaction time will vary from about 5 to about 15 hr for small quantities of product.

The 3,5-DHPZNA product is readily isolated from the reaction mass by filtration, and washing the filtrate with aqueous inorganic acid, typically HCl or H$_2$SO$_4$. The filtrate is dried with a dessicant such as sodium sulfate, then heated to dryness. The product obtained may be recrystallized from a solvent if greater purity is desired.

The structure of the 3,5-DHPZNA product is confirmed by elemental analysis for carbon and hydrogen, and infrared (IR) and nuclear magnetic resonance (NMR) spectra. Molecular weights were determined and confirmed by field desorption mass spectra (FD/MS).

EXAMPLE 1

A. Preparation of N-isopropyl-N-[2-(2-keto-3,3,5,5-tetramethyl-1-piperazinyl)ethyl]-2-(3,5-di-t-butyl-4-hydroxyphenyl)-2-methyl-propanamide represented by the structure

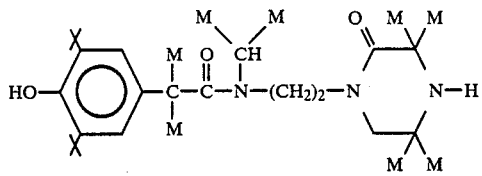

M=methyl 0.1 Mole of 2,6-di-t-butylphenol, 1.0 mole of acetone, 0.15 mole of chloroform, and 0.1 mole of N'-(2-isopropylaminoethyl-3,3,5,5-tetramethyl-2-piperazinone are added to a reactor and mixed by stirring while being cooled in a circulating ice-cold bath. 0.5 mole of powdered NaOH is slowly added over a period of 1 hr. The reaction mixture is stirred at 10° C. overnight. The reaction mix from the reactor is filtered, the solid residue washed with methylene chloride, and the wash added to the filtrate. The filtrate is washed with 50 ml of 4N hydrochloric acid, 50 ml of 5% sodium carbonate, then dried over sodium sulfate. The filtrate is evaporated to dryness and the dried product is washed with hexane. The resulting amide is a white solid with a melting point of 165°-169° C. and a molecular weight of 515. By elemental analysis it is determined that the amide contained 72.43% carbon (72.19% calculated), 10.26% hydrogen (calculated 10.36%) and 8.02% nitrogen (calculated 8.15%).

B. N'-(2-isopropylaminoethyl-3,3,5,5-tetramethyl-2-piperazinone is reduced to yield the corresponding piperazine which is then reacted in a manner analogous to that described hereinabove in 1A, to produce N-isopropyl-N-[2-(3,3,5,5-tetramethyl-1-piperazinyl)ethyl]-2-(3,5-di-t-butyl-4-hydroxyphenyl)-2-methyl-propanamide.

EXAMPLE 2

A. Preparation of N-[1-(2-keto-3,3,5,5-tetramethyl-1-piperazinyl-2-methyl-2-propyl]-2-(3,5-di-t-butyl-4-hydroxyphenyl)-2-methyl-propanamide represented by the structure

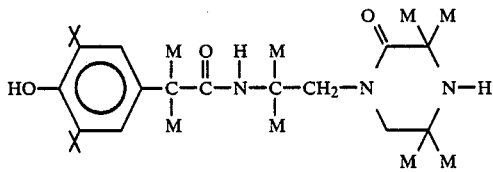

0.1 mol of imino-bis-(2-amino-2-methyl-1 propane), 0.15 mol chloroform and 2.0 mols of acetone were placed in a 3-neck flask equipped with a thermometer, a mechanical stirrer, cooling means and an addition funnel. The mixture is kept cool in a circulating ice-bath, while 0.5 mol- of NaOH beads are added in small portions to keep the reaction temperature below 10° C. After the addition, the reaction is stirred under nitrogen until a GC (gas chromatographic) analysis of a sample shows the reaction of the amine is substantially complete. 0.14 mols of chloroform and 0.1 mole of 2,6-di-t-butylphenol are added, followed by 0.5 mole of NaOH beads in portions to keep the temperature below 10° C. The mixture is stirred at 10° C. overnight. The mass is concentrated in a rotary evaporator to remove solvents and low boilers and stirred in a hexanes-water mixture. The solid is collected and washed with hexanes and water. The yield is about 70% after drying. The substituted propanamide is recrystallized from 70% ethanol with a few drops of 85% hydrazine to yield white crystals. The melting point is 145°-8° C.

B. In a manner analogous to that described hereinabove in 1B, the corresponding piperazine is reacted to produce N-[1-(3,3,5,5-tetramethyl-1-piperazinyl-2-methyl-2-propyl]-2-(3,5-di-t-butyl-4-hydroxyphenyl)-2-methyl-propanamide.

EXAMPLE 3

A. Preparation of N-[1-(2-keto-3,5,5-trimethyl-3-ethyl-1-piperazinyl-2-methyl-2-propyl]-2-(3,5-di-t-butyl-4-hydroxyphenyl)-2-methyl-butanamide represented by the structure

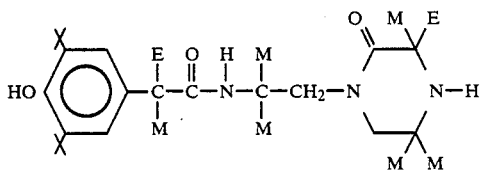

E=ethyl

In a manner analogous described in example 2 hereinabove, but replacing the ketone used therein with 2 mols of butanone, a substituted butanamide is obtained which is represented by the structure immediately hereinabove, and has a melting point of 126°-8° C.

B. In a manner analogous to that described hereinabove in 1B, the corresponding piperazine is reacted to produce N-[1-(3,5,5-trimethyl-3-ethyl-1-piperazinyl-2-methyl-2-propyl]-2-(3,5-di-t-butyl-4-hydroxyphenyl)-2-methylbutanamide.

EXAMPLE 4

A. Preparation of N-[1-(2-keto-3,3-pentamethylene-5,5-dimethyl-1-piperazinyl)-2-methyl-2-propyl]-2-(3,5-di-t-butyl-4-hydroxyphenyl)-2,2-pentamethylene acetamide represented by the structure

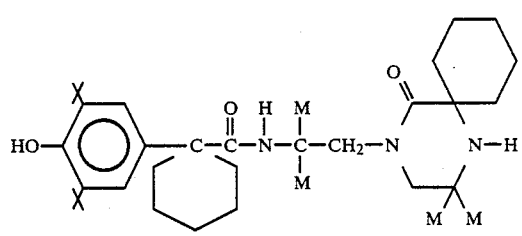

In a manner analogous described in example 2 hereinabove, but replacing the ketone used therein with 2 mols of cyclohexanone, a substituted acetamide is obtained which is represented by the structuree immediately hereinabove, and has a melting point of 179°-182° C.

B. In a manner analogous to that described hereinabove in 1B, the corresponding piperazine is reacted to produce N-[1-(3,3-pentamethylene-5,5-dimethyl-1- piperazinyl)-2-methyl-2-propyl]-2-(3,5-di-t-butyl-4-hydroxyphenyl)-2,2-pentamethylene acetamide.

EXAMPLE 5

A. Preparation of N-[1-(2-keto-3,3,5,5-tetramethyl-1-piperazinyl-2-methyl 2-propyl]-2-(3,5-di-t-butyl-4-hydroxyphenyl)-2,2-pentamethylene acetamide represented by the structure

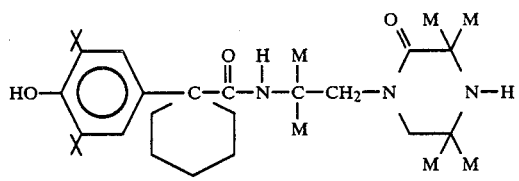

In a manner analogous to that described in example 2 hereinabove, but replacing the substituted piperazinone used therein with 0.1 mol of N¹-(2-amino-2-methyl-1-propyl)-3,3,5,5-tetramethyl-2-piperazinone, the substituted acetamide represented by the structure immediately hereinabove is obtained as an off-white colored powder by recrystallization from hexanes and has a melting point of 125°–130° C.

B. In a manner analogous to that described hereinabove in 1B, the corresponding piperazine is reacted to produce N-[1-(3,3,5,5-tetramethyl-1-piperazinyl-2-methyl 2-propyl]-2-(3,5-di-t-butyl-4-hydroxyphenyl)-2,2-pentamethylene acetamide.

EXAMPLE 6

A. Preparation of N-cyclohexyl-N-[2-(2-keto-3,3,5,5-tetramethyl-1-piperazinyl ethyl]-2-(3,5-di-t-butyl-4-hydroxyphenyl)-2,2-pentamethylene acetamide represented by the structure

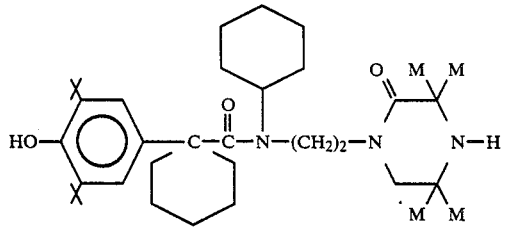

In a manner analogous described in example 2 hereinabove, but replacing the substituted piperazinone used therein with 0.1 mol of N¹-(2-cyclohexylaminoethyl)-3,3,5,5-tetramethyl-2-piperazinone, the substituted acetamide represented by the structure immediately hereinabove is obtained as an off-white colored powder by recrystallization from hexanes and has a melting point of 60° C.

B. In a manner analogous to that described hereinabove in 1B, the corresponding piperazine is reacted to produce N-cyclohexyl-N-[2-(3,3,5,5-tetramethyl-1-piperazinyl ethyl]-2-(3,5-di-t-butyl-4-hydroxyphenyl)-2,2-pentamethylene acetamide.

EXAMPLE 7

A. Preparation of N-cyclohexyl-N-[3-(2-keto-3,3,5,5-tetramethyl-1-piperazinyl propyl]-2-(3,5-di-t-butyl-4-hydroxyphenyl)-2,2-pentamethylene acetamide represented by the structure

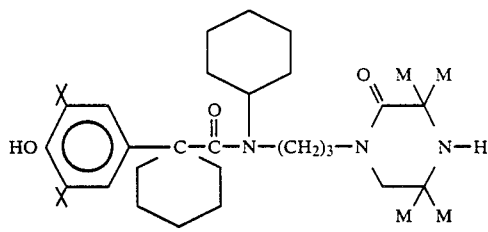

In a manner analogous described in example 2 hereinabove, but replacing the substituted piperazinone used therein with 0.1 mol of N¹-(2-cyclohexylamino-1-propyl)-3,3,5,5-tetramethyl-2-piperazinone, the substituted acetamide represented by the structure immediately hereinabove is obtained as a powder by recrystallization from hexanes, and has a melting point of 60° C.

B. In a manner analogous to that described hereinabove in 1B, the corresponding piperazine is reacted to produce N-cyclohexyl-N-[3-(3,3,5,5-tetramethyl-1-piperazinyl propyl]-2-(3,5-di-t-butyl-4-hydroxyphenyl)-2,2-pentamethylene acetamide.

EXAMPLE 8

A. Preparation of N-cyclohexyl-N-[3-(2-keto-3,3,5,5-tetramethyl-1-piperazinyl-propyl]-2-(3,5-di-t-butyl-4-hydroxyphenyl)-2-methyl propanamide represented by the structure

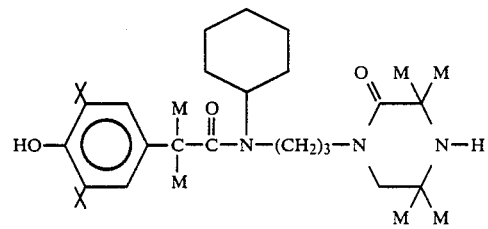

In a manner analogous to that described in example 2 hereinabove, but replacing the substituted piperazinone used therein with 0.1 mol of N¹-(2-amino-2-methyl-1-propyl)-3,3,5,5-tetramethyl-2-piperazinone, the substituted acetamide represented by the structure immediately hereinabove is obtained as a powder by recrystallization of hexanes and has a melting point of 172°–174° C.

B. In a manner analogous to that described hereinabove in 1B, the corresponding piperazine is reacted to produce N-cyclohexyl-N-[3-(3,3,5,5-tetramethyl-1-piperazinylpropyl]-2-(3,5-di-t-butyl-4-hydroxyphenyl)-2-methyl propanamide.

EXAMPLE 9

A. Preparation of N-cyclohexyl-N-[3-(2-keto-3,3,5,5-tetramethyl-1-piperazinyl-propyl]-2-(3,5-di-t-butyl-4-hydroxyphenyl)-2-methyl butanamide represented by the structure

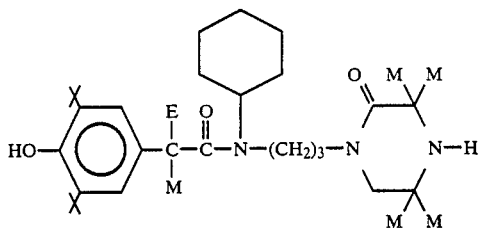

In a manner analogous to that described in example 2 hereinabove, but replacing the ketone used therein with 2 mols of 2-butanone, a substituted acetamide is obtained which is represented by the structure immediately hereinabove, and has a melting point of 118°–121° C.

B. In a manner analogous to that described hereinabove in 1B, the corresponding piperazine is reacted to produce N-cyclohexyl-N-[3-(3,3,5,5-tetramethyl-1-piperazinylpropyl]-2-(3,5-di-t-butyl-4-hydroxyphenyl)-2-methyl butanamide.

To demonstrate the stabilizing activity of the 3,5-DHPZNA compounds, test samples of polypropylene in which each of the compounds is homogeneously dispersed, are prepared as described hereinbefore.

The following results were obtained for thermal/oxidative stability at 125° C., given in "days to failure" judged by crumbling, for compositions stabilized with specific 3,5-DHPZNA stabilizers:

|  | Days |
| --- | --- |
| Control (blank) | 2 |
| Compound 1A (made in example 1A herebelow) N—isopropyl-N—[2-(2-keto-3,3,5,5-tetramethyl-1-piperazinyl)ethyl]-2-(3,5-di-t-butyl-4-hydroxyphenyl)-2-methyl propanamide | 9 |

It is evident from the foregoing that the thermal/oxidative stabilizing activity of the 3,5-DHPZNA compounds is lower than that of commercially available materials with two unsubstituted carbon atoms in the link to the hydroxyphenyl ring, such as tris-[3,5-di-t-butyl-4-hydroxyphenyl]-isocyanurate, but 3,5-DHPZNA do contribute to the overall stabilizing power of the compounds and are surprisingly effective against degradation by ultraviolet light.

Samples of PP containing the foregoing stabilizers were also tested for uv stabilizing activity, in the manner described hereinabove. The time to degradation severe enough to cause a 50% loss of tensile strength, is given in hrs. As before, the control was a blank containing no stabilizer.

|  | hrs. |
| --- | --- |
| Control (blank) | 220 |
| Compound 1A (made in example 1A herebelow) N—isopropyl-N—[2-(2-keto-3,3,5,5-tetramethyl-1-piperazinyl)ethyl]-2-(3,5-di-t-butyl-4-hydroxyphenyl)-2-methyl propanamide | 1280 |

The 3,5-DHPZNA stabilizers of this invention provide an exceptional combination of heat stability and resistance to uv degradation when used in polyolefin resins. They aree especially effective stabilizers in α-monoolefin homopolymers and copolymers, wherein the α-monoolefin contains 2 to about 8 carbon atoms. High and low density polyethylene, isotactic and atactic polypropylene, polyisobutylene, and poly(4-methyl-1-pentene) have excellent resistance to heat and oxygen when stabilzed with combinations of stabilizers of this invention. Ethylene-propylene copolymers and ethylene-propylene terpolymers, generally containing less than about 10 percent by weight of one or more monomers containing multiple unsaturation provided by, for example, 1,4-hexadiene, dimethyl-1,4,9-decatriene, dicyclopentadiene, vinyl norbornene, ethylidene norbornene, and the like, also provide excellent aging using conbinations of the stabilizers.

By "combination of stabilizers of this invention" I refer not only to combinations of the 3,5-DHPZNA stabilizers which might be more effective than a single 3,5-DHPZNA stabilizer, but also more particularly, to combinations of a 3,5-DHPZNA stabilizer with known stabilizers, some of which are identified hereafter, for a specific organic material sought to be stabilized in the environment in which it is to be used.

Organic materials which may be stabilized against uv light, thermal and oxidative degradation, include copolymers of butadiene with acrylic acid, alkyl acrylates or methacrylates, polyisoprene, polychloroprene, and the like; polyurethanes; vinyl polymers known as PVC resins such as polyvinyl chloride, copolymers of vinyl chloride with vinylidene chloride, copolymers of vinyl halide with butadiene, styrene, vinyl esters, and the like; polyamides such as those derived from the reaction of hexamethylene diamine with adipic or sebacic acid; epoxy resins such as those obtained from the condensation of epichlorohydrin with bisphenols, and the like; ABS resins, polystyrene, polyacrylonitrile, polymethacrylates, polycarbonates, varnish, phenol-formaldehyde resins, polyepoxides, polyesters, and polyolefin homo- and copolymers such as polyethylene, polypropylene, ethylene-propylene polymers, ethylene-propylenediamine polymers, ethylene vinyl acetate polymers and the like. The 3,5-DHPZNA stabilizers can also be used to stabilize mixtures and blends of oligomeric materials such as ABS resin blends, PVC and polymethacrylate blends, and blends of homopolymers and copolymers such as blends of polypropylene in EPDM polymers.

Most particularly, the 3,5-DHPZNA stabilizers are especially useful as uv-light stabilizers for synthetic resinous materials used in the form of fibers, or in thermoformed shaped articles which are at least partially permeable to visible light, and particularly for those articles which are transparent thereto, such as those made from polyvinylaromatics and polyolefins.

The excellent compatibility of 3,5-DHPZNAs with phenolic antioxidants allows the latter to be used as secondary stabilizers in a mixture which enhances the stability of the composition in which the mixture is used, with predictably good results. When so used, the phenolic AOs preferably range from about 0.1 to about 5 phr of the material to be stabilized. Such hindered phenol AOs are 2,6-di-t-butyl-paracresol; 2,2'-methylene-bis(6-t-butyl-phenol); 2,2'-thiosbis(4-methyl-6-t-butyl-phenol); 2,2'-methylene-bis(6-t-butyl-4-ethyl-phenol); 4,4'-butylidene-bis(6-t-butyl-m-cresol); 2-(4-hydroxy-3,5-di-t-butylanilino)-4,6-bis(octylthio)-1,3,5-triazine; benzenepropanoic acid, 3,5-bis(1,1-dimethylethyl)-4-hydroxy-,(2,4,6-trioxo-1,3,5-triazine-1,3,5(2H,4H,6H)-triyl)tri-2,1-ethanediyl ester (Goodrite®3125); tetrakis[methylene 3-(3',5'-di-t-butyl-4'- hydroxyphenyl)propionate]methane; and particularly commercially available antioxidants such as Irganox 1010, 1035, 1076 and 1093.

Of the other types of AOs used, are the phosphite, o-hydroxy-benzophenone, benzotriazole, and sulfide AOs, the first three generic types having the effect of boosting the uv stability of the composition most unexpectedly.

The 3,5-DHPZNAs are found to be highly effective stabilizers in polpropylene fibers, as evidenced by the test results set forth below for samples in which the 3,5-DHPZNA was combined with 0.1 hr calcium stearate, 0.1 phr of tris(3,5-di-t-butyl-4-hydroxybenzyl-)isocyanurate and blended into 100 parts of Profax PP. The stabilized PP is pelletized and spun into fiber which is tested in a Weather-O-Meter for hours to failure.

|  | Hrs. |
|---|---|
| Control sample with tris(3,5-di-t-butyl-4-hydroxybenzyl)isocyanurate (0.1 phr) | 260 |
| Test sample 3, with | |
| N—[1-(2-keto-3,3,5,5-tetramethyl-1-piperazinyl)-2-methyl-2-propyl]-2-(3,5-di-t-butyl-4-hydroxyphenyl)-2-methyl-propanamide | 1080 |
| Test sample 4, with | |
| N—[1-(2-keto-3,3-pentamethylene-5,5-dimethyl-1-piperazinyl)-2-methyl-2-propyl]-2-(3,5-di-t-butyl-4-hydroxyphenyl)-2,2-pentamethylene acetamide | 980 |
| Test sample 5, with | |
| N—cyclohexyl-N—[3-(2-keto-3,3,5,5-tetramethyl-1-piperazinyl-propyl]-2-(3,5-di-t-butyl-4-hydroxyphenyl)-2-methyl propanamide | 530 |

The 3,5-DHPZNA stabilizers are particularly effective with secondary stabilizers in polypropylene (PP), as evidenced by the following tests on PP samples in which from about 0.05 phr to 5 phr of the 3,5-DHPZNA being tested, and from 0.05 phr to 5 phr of a secondary stabilizer, preferably with a processing aid, and/or lubricant, such as calcium stearate, are mixed into the PP until homogeneously distributed.

|  | Hrs. |
|---|---|
| Control (blank) -undecane 2,2',2"-tris[3(3,5-di-t-butyl-4-hydroxyphenyl)propionyloxy]ethyl isocyanurate (0.05 phr) | 340 |
| Test sample 1 | |
| N—isopropyl-N—[2-(2-keto-3,3,5,5-tetramethyl-1-piperazinyl)ethyl]-2-(3,5-di-t-butyl-4-hydroxyphenyl)-2-methyl propanamide, (0.05 phr) and 1,1'-(1,2-ethanediyl)bis(3,3,5,5-tetramethyl-1-piperazinone, (0.05 phr) and 2,2',2"-tris[3(3,5-di-t-butyl-4-hydroxyphenyl)propionyloxy]ethyl isocyanurate (0.05 phr) | >2000 |
| Test sample 2 | |
| N—isopropyl-N—[2-(2-keto-3,3,5,5-tetramethyl-1-piperazinyl)ethyl]-2-(3,5-di-t-butyl-4-hydroxyphenyl)-2-methyl propanamide, (0.125 phr) and 3,9-bis(octadecyloxy)-2,4,8,10-teraoxa-3,9-diphospha-spiro[5,5,5]-undecane (0.125 phr) and 2,2',2"-tris[3(3,5-di-t-butyl-4-hydroxyphenyl)propionyloxy]ethyl isocyanurate (0.05 phr) | >2000 |

Certain 3,5-DHPZNAs are found to be more effective as uv light stabilizers than as antioxidants, and others are found to have substantially better antioxidant activity. Therefore, a combination of 3,5-DHPZNAs may be used. Even more effective than a combination of 3,5-DHPZNAs is a combination of a 3,5-DHPZNA with another stabilizer, sometimes referred to as a secondary stabilizer, selected from diphosphites, triaryl phosphites and o-hydroxy-benzophenones or 2-hydroxyphenylbenzotriazole compounds, known to be effective stabilizers for specific synthetic resinous materials, particularly those derived from an acyclic hydrocarbon with single unsaturation.

A stabilized composition of matter is most preferably
(a) a polymer which is derived from a singly unsaturated acyclic hydrocarbon, or mixtures or copolymers thereof, in which is dispersed
(b) from 0.05 to 5 parts per hundred parts by weight of the polymer, of a mixture of
(i) the 3,5-DHPZNA, and,
(ii) from 0.05 to about 5 phr of another stabilizer selected from the group consisting of a (a) bis-(dialkylphenyl)pentaerythritol diphosphite, (b) triarylphosphite, (c) o-hydroxy-benzophenone, and (d) a 2-hydroxyphenylbenzotriazole,
said diphosphite represented by the structure

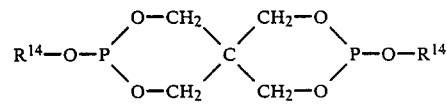

wherein $R^{14}$ is $C_3$-$C_{24}$ alkyl, or di-($C_3$-$C_9$)alkylphenyl; said triarylphosphite represented by the structure

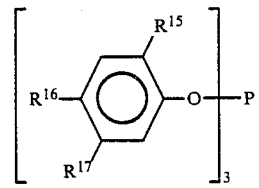

wherein $R^{15}$ represents t-butyl, 1,1-dimethylpropyl, cyclohexyl or phenyl, and one of $R^{16}$ and $R^{17}$ is hydrogen and the other is hydrogen, methyl, t-butyl, 1,1-dimethylpropyl, cyclohexyl or phenyl;
said o-hydroxy-benzophenone represented by the structure

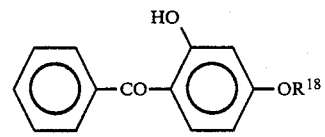

wherein $R^{18}$ is $C_1$-$C_{24}$ alkyl, and,
said 2-hydroxyphenylbenzotriazole represented by the structure,

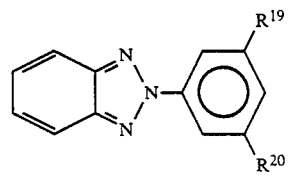

wherein $R^{19}$ is lower alkyl or halogen (preferably chlorine); $R^{20}$ is lower alkyl, halogen (preferably chlorine), or hydrogen; and, X is chlorine or hydrogen; the ratio of the 3,5-DHPZNA to the secondary stabilizer being in the range from about 5:1 to about 1:5.

For example, a commercially available disphosphite such as bis-(2,4-di-t-butylphenyl)pentaerythritol disphosphite, or distearyl pentaerythritol disphosphite, may be used in combination with about the same amount of the 3,5-DHPZNA; or, a commercially available triarylphosphite such as tris-(2,5-di-t-butylphenyl)-phosphite, tris-(2-t-butylphenyl)-phosphite, tris-(2-t-phenylphenyl)-phosphite, tris-[(2-1,1-dimethylpropyl)-phenyl]-phosphite, tris-(2,4-di-t-butylphenyl)-phosphite, and the like; or, a commercially available benzophenone such as 2-hydroxy-4-n-octoxybenzophenone in combination with about the same amount of the 3,5-DHPZNA; or, a commercially available benzotriazole such as 2-(2'-hydroxy-3',5'-di-t-butylphenyl)-5-chlorobenzotriazole (Tinuvin 327), 2-(2'-hydroxy-3'-t-butyl-5'-methylphenyl)benzotriazole (Tinuvin 326), 2-(2'-hydroxy-5'-methylphenyl)benzotriazole (Tinuvin P), 2-(2'-hydroxy-3',5'-dimethylphenyl)-5-chlorobenzotriazole, 2-(2'-hydroxy-3',5'-di-t-octylphenyl)benzotriazole (Tinuvin 328), and the like, in combination with about the same amount of the 3,5-DHPZNA.

It is found that, when the 3,5-DHPZNA is used in combination with one of (a) bis-(alkyl) or bis-(dialkylphenyl)pentaerythritol diphosphite, (b) triarylphosphite, (c) o-hydroxy-benzophenone, and (d) a 2-hydroxyphenylbenzotriazole, there is an unexpectedly greater increase in stability of a synthetic resinous material to degradation by uv light, and very often, also to thermal-/oxidative degradation, than one might be led to expect from the cumulative effectiveness of each stabilizer used separately. For example, the stability one obtains with a mixture of 0.125 phr of a 3,5-DHPZNA and 0.125 phr of one of the specific secondary stabilizers, one gets much greater stability than with 0.25 phr (the same weight) of a 3,5-DHPZNA. This is most unexpected because the stabilization of such stabilizers is closely correlatable to the weight (phr) of stabilizer used.

The 3,5-DHPZNAs, such as secondary stabilizers as may be desired, and other compounding ingredients if used, can be admixed with the synthetic resinous material to be stabilized using known mixing techniques and equipment such as internal mixing kettles, a Banbury mixer, a Henschel mixer, a two-roll mill, an extruder mixer, or other standard equipment, to yield a composition which may be extruded, presed, blowmolded or the like into film, fiber or shaped articles. Usual mixing times and temperatures can be employed which may be determined with a little trial and error for any particular composition. The objective is to obtain intimate and uniform mixing of the components. A favorable mixing procedure to use when adding a 3,5-DHPZNA to an organic material is either to dissolve or suspend the 3,5-DHPZNA in a liquid such as methylene chloride before adding it, or to add the 3,5-DHPZNA directly to the synthetic resinous material whether the 3,5-DHPZNA is in the form of a powder or oil, or to extruder-mix the 3,5-DHPZNA and material prior to forming the product.

Many known compoundng ingredients may be used along with the 3,5-DHPZNAs, or combinations thereof with secondary stabilizers, in the synthetic resinous compositions. Such ingredients include lubricant metal oxides such as zinc, calcium and magnesium oxide, fatty acids such as stearic and lauric acid, and salts thereof such as cadmium, zinc and sodium stearate and lead oleate; filler such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearates, sebacates, azelates, phthalates, and the like; ASTM type 2 petroleum oils, paraffinic oils, castor oil, tall oil, glycerin and the like.

Other ingredients such as pigments, tackifiers, flame retardants, fungicides, and the like may also be added.

The stabilized resin composition may then be thermoformed by extrusion, injection molding, blow molding and the like, into a wide variety of articles ranging from flexible or rigid laminar sheets, self-supporting films, filament, and articles of arbitrary shape.

We claim:

1. A N-(substituted)-1-(piperazinealkyl)-α-(3,5-dialkyl-4-hydroxyphenyl)-α,α-substituted acetamide, represented by the structure

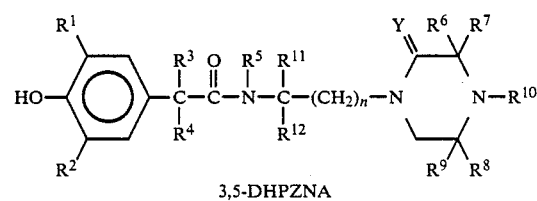

3,5-DHPZNA wherein,
$R^1$, $R^2$ and $R^5$ each represent hydrogen, $C_1$–$C_{12}$ alkyl, phenyl, naphthyl, $C_4$–$C_{12}$ cycloalkyl, and alkyl-substituted cycloalkyl, phenyl and naphthyl, each alkyl substituent being $C_1$–$C_8$, and at least one of $R^1$ and $R^2$ is t-$C_4$–$C_{12}$ alkyl;

$R^3$ and $R_4$ independently represent $C_1$–$C_{18}$ alkyl, and $C_5$–$C_{12}$ cycloalkyl, phenyl and naphthyl, and, alkyl-substituted cycloalkyl, phenyl and naphthyl, each alkyl substituent being $C_1$–$C_8$, and, when together cyclized, $R^3$ with $R^4$ may represent $C_4$–$C_{12}$ cycloalkyl, and $C_1$–$C_8$ alkyl-substituted cycloalkyl;

$R^6$, $R^7$, $R^8$ and $R^9$ each represent $C_1$–$C_{12}$ alkyl, or, when together cyclized, $R^6$ with $R^7$, and $R^8$ with $R^9$, may represent $C_4$–$C_{12}$ cycloalkyl, and $C_1$–$C_8$ alkyl-substituted cycloalkyl;

$R^{10}$ is selected from the group consisting of hydrogen, $C_1$–$C_8$ alkyl and

wherein
$R^{13}$ represents hydrogen, $C_1$–$C_{18}$ alkyl or alkenyl, phenyl or naphthyl;
$R^{11}$ and $R^{12}$ independently represent hydrogen and $C_1$–$C_{18}$ alkyl;
n is an integer in the range from 1 to about 8; and,
Y represents $H_2$ when the diazacycloalkane ring is piperazinyl, and O when the diazacycloalkane ring represents piperazin-2-one.

2. The 3,5-DHPZNA of claim 1 wherein,
n is 2 or 3, and Y is oxygen, O;
$R^1$ is $C_1$–$C_8$ alkyl, $R^2$ is $C_1$–$C_5$ alkyl,
$R^3$ and $R^4$ are each $C_1$–$C_8$ alkyl, and together, when cyclized represent cyclohexyl, methylcyclohexyl, cycloheptyl;

R⁵ is C₁–C₈ alkyl; and,
R¹⁰ is hydrogen or C₁–C₈ alkyl.

3. The 3,5-DHPZNA of claim 2 wherein,
at least one of R¹ and R² is t-butyl, or t-amyl; and,
R³ and R⁴ are each C₁–C₄ alkyl.

4. The 3,5-DHPZNA of claim 1 wherein,
n is 2 or 3, and Y is hydrogen, H₂;
R¹ is C₁–C₈ alkyl, R² is C₁–C₅ alkyl,
R³ and R⁴ are each C₁–C₈ alkyl, and together, when cyclized represent cyclohexyl, methylcyclohexyl, cycloheptyl;
R⁵ is C₁–C₈ alkyl; and,
R¹⁰ is hydrogen or C₁–C₈ alkyl.

5. The 3,5-DHPZNA of claim 4 wherein,
at least one of R¹ and R² is t-butyl, or t-amyl; and,
R³ and R⁴ are each C₁–C₄ alkyl.

6. The 3,5-DHPZNA of claim 2 selected from the group consisting of
(1) N-isopropyl-N-[2-(2-keto-3,3,5,5-tetramethyl)-1-piperazinyl)ethyl]-2-(3,5-di-t-butyl-4-hydroxyphenyl)-2-methyl-propanamide
(2) N-[1-(2-keto-3,3,5,5-tetramethyl-1-piperaznyl-2-methyl-2-propyl]-2-(3,5-di-t-butyl-4-hydroxypheny)-2-methyl-propanamide
(3) N-[1-(2-keto-3,5,5-trimethyl-3-ethyl-1-piperazinyl-2-methyl-2-propyl]-2-(3,5-di-t-butyl-4-hydroxyphenyl)-2-methyl-butanamide
(4) N-[1-(2-keto-3,3-pentamethylene-5,5-dimethyl-1-piperazinyl)-2-methyl-2-propyl]-2-(3,5-di-t-butyl-4-hydroxyphenyl)-2,2-pentamethylene acetamide
(5) N-[1-(2-keto-3,3,5,5-tetramethyl-1-piperazinyl-2-methyl 2-propyl]-2-(3,5-di-t-butyl-4-hydroxyphenyl)-2,2-pentamethylene acetamide
(6) N-cyclohexyl-N-[2-(2-keto-3,3,5,5-tetramethyl-1-piperazinyl ethyl]-2-(3,5-di-t-butyl-4-hydroxyphenyl)-2,2-pentamethylene acetamide
(7) N-cyclohexyl-N-[3-(2-keto-3,3,5,5-tetramethyl-1-piperazinyl propyl]-2-(3,5-di-t-butyl-4-hydroxyphenyl)-2,2-pentamethylene acetamide
(8) N-cyclohexyl-N-[3-(2-keto-3,3,5,5-tetramethyl-1-piperazinyl-propyl]-2-(3,5,-di-t-butyl-4-hydroxyphenyl)-2-methyl propanamide
(9) N-cyclohexyl-N-[3-(2-keto-3,3,5,5-tetramethyl-1-piperazinyl-propyl]-2-(3,5-di-t-butyl-4-hydroxyphenyl)-2-methyl butanamide.

7. The 3,5-DHPZNA of claim 4 selected from the group consisting of
(1) N-isopropyl-N-[2-(3,3,5,5-tetramethyl-1-piperazinyl-)ethyl]-2-(3,5-di-t-butyl-4-hydroxyphenyl)-2-methyl-propanamide
(2) N-[1-(3,3,5,5-tetramethyl-1-piperazinyl-2-methyl-2-propyl]-2-(3,5-di-t-butyl-4-hydroxyphenyl)-2-methyl-propanamide
(3) N-[1-(3,5,5-trimethyl-3-ethyl-1-piperazinyl-2-methyl-2-propyl]-2-(3,5-di-t-butyl-4-hydroxyphenyl)-2-methylbutanamide
(4) N-[1-(3,3-pentamethylene-5,5-dimethyl-1-piperazinyl)-2-methyl-2-propyl]-2-(3,5-di-t-butyl-4-hydroxyphenyl)-2,2-pentamethylene acetamide
(5) N-[1-(3,3,5,5-tetramethyl-1-piperazinyl-2-methyl 2-propyl]-2-(3,5-di-t-butyl-4-hydroxyphenyl)-2,2-pentamethylene acetamide
(6) N-cyclohexyl-N-[2-(3,3,5,5-tetramethyl-1-piperazinyl ethyl]-2-(3,5-di-t-butyl-4-hydroxyphenyl)-2,2-pentamethylene acetamide
(7) N-cyclohexyl-N-[3-(3,3,5,5-tetramethyl-1-piperazinyl propyl]-2-(3,5-di-t-butyl-4-hydroxyphenyl)-2,2-pentamethylene acetamide
(8) N-cyclohexyl-N-[3-(3,3,5,5-tetramethyl-1-piperazinylpropyl]-2-(3,5-di-t-butyl-4-hydroxyphenyl)-2-methyl propanamide
(9) N-cyclohexyl-N-[3-(3,3,5,5-tetramethyl-1-piperazinylpropyl]-2-(3,5-di-t-butyl-4-hydroxyphenyl)-2-methyl butanamide.

8. A stabilized composition of matter comprising an organic material subject to degradation, in which material is dispersed from 0.05 to 5 parts per hundred parts by weight of the material, of a N-(substituted)-1-(piperazinealkyl)-α-(3,5-dialkyl-4-hydroxyphenyl)-α,α-substituted acetamide, represented by the structure

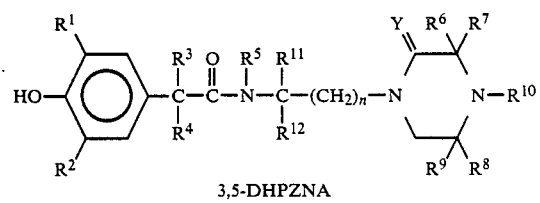

3,5-DHPZNA wherein,
R¹, R² and R⁵ each represent hydrogen, C₁–C₁₂ alkyl, phenyl, naphthyl, C₄–C₁₂ cycloalkyl, and, alkyl-substituted cycloalkyl, phenyl and naphthyl, each alkyl substituent being C₁–C₈, and at least one of R¹ and R² is t-C₄–C₁₂ alkyl;
R³ and R⁴ independently represent C₁–C₁₈ alkyl, and C₅–C₁₂ cycloalkyl, phenyl and naphthyl, and, alkyl-substituted cycloalkyl, phenyl and naphthyl, each alkyl substituent being C₁–C₈, and, when together cyclized, R³ with R⁴ may represent C₄–C₁₂ cycloalkyl, and C₁–C₈ alkyl-substituted cycloalkyl;
R⁶, R⁷, R⁸ and R⁹ each represent C₁–C₁₂ alkyl, or, when together cyclized, R⁶ with R⁷, and R⁸ with R⁹, may represent C₄–C₁₂ cycloalkyl, and C₁–C₈ alkyl-substituted cycloalkyl;
R¹⁰ is selected from the group consisting of hydrogen, C₁–C₈ alkyl and

wherein
R¹³ represents hydrogen, C₁–C₁₈ alkyl or alkenyl, phenyl or naphthyl;
R¹¹ and R¹² independently represent hydrogen and C₁–C₁₈ alkyl;
n is an integer in the range from 1 to about 8; and,
Y represents H₂ when the diazacycloalkene ring is piperazinyl, and O when the diazacycloalkane ring represents piperazin-2-one.

9. The stabilized composition of matter of claim 8 wherein said 3,5-DHPZNA is characterized by,
n is 2 or 3, and Y is oxygen, O;
R¹ is C₁–C₈ alkyl, R² is C₁–C₅ alkyl,
R³ and R⁴ are each C₁–C₈ alkyl, and together, when cyclized represent cyclohexyl, methylcyclohexyl, cycloheptyl;
R⁵ is C₁–C₈ alkyl; and,
R¹⁰ is hydrogen or C₁–C₈ alkyl.

10. A method of stabilizing a synthetic resinous material derived from a singly unsaturated acyclic hydrocarbon, or mixtures of copolymers thereof, during processing said material, which method comprises incorporating in said material a mixture comprising (i) from 0.05 to 5 phr of a N-(substituted)-1-(piperazinealkyl)-α-(3,5-dialkyl-4-hydroxyphenyl)-α,α-substituted acetamide, represented by the structure

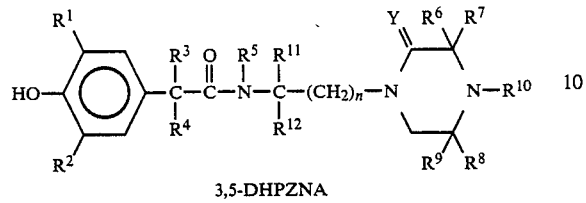

3,5-DHPZNA wherein, $R^1$, $R^2$ and $R^5$ each represent hydrogen, $C_1$–$C_{12}$ alkyl, phenyl, naphthyl, $C_4$–$C_{12}$ cycloalkyl, and, alkyl-substituted cycloalkyl, phenyl and naphthyl, each alkyl substituent being $C_1$–$C_8$, and at least one of $R^1$ and $R^2$ is t-$C_4$–$C_{12}$ alkyl;

$R^3$ and $R^4$ independently represent $C_1$–$C_{18}$ alkyl, and $C_5$–$C_{12}$ cycloalkyl, phenyl and naphthyl, and, alkyl-substituted cycloalkyl, phenyl and naphthyl, each alkyl substituent being $C_1$–$C_8$, and, when together cyclized, $R^3$ with $R^4$ may represent $C_4$–$C_{12}$ cycloalkyl, and $C_1$–$C_8$ alkyl-substituted cycloalkyl;

$R^6$, $R^7$, $R^8$ and $R^9$ each represent $C_1$–$C_{12}$ alkyl, or, when together cyclized, $R^6$ with $R^7$, and $R^8$ with $R^9$, may represent $C_4$–$C_{12}$ cycloalkyl, and $C_1$–$C_8$ alkyl-substituted cycloalkyl;

$R^{10}$ is selected from the group consisting of hydrogen, $C_1$–$C_8$ alkyl and

wherein $R^{13}$ represents hydrogen, $C_1$–$C_{18}$ alkyl or alkenyl, phenyl or naphthyl;

$R^{11}$ and $R^{12}$ independently represent hydrogen and $C_1$–$C_{18}$ alkyl;

n is an integer in the range from 1 to about 8; and,

Y represents $H_2$ when the diazacycloalkane ring is piperazinyl, and O when the diazacycloalkane ring represents piperazin-2-one;

(ii) from 0.05 to about 5 phr of another stabilizer selected from the group consisting of a (a) bis-(dialkylphenyl)pentaerythritol diphosphite, (b) triarylphosphite, (c) o-hydroxy-benzophenone, and (d) a 2-hydroxyphenylbenzotriazole, said diphosphite represented by the structure

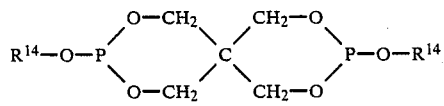

wherein $R^{14}$ is $C_3$–$C_{24}$ alkyl, or di-($C_3$–$C_9$)alkylphenyl;

said triarylphosphite represented by the structure

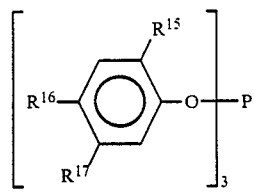

wherein $R^{12}$ represents t-butyl, 1,1-dimethylpropyl, cyclohexyl or phenyl, and one of $R^{13}$ and $R^{14}$ is hydrogen and the other is hydrogen, methyl, t-butyl, 1,1-dimethylpropyl, cyclohexyl or phenyl;

said o-hydroxy-benzophenone represented by the structure

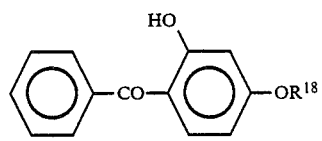

wherein $R^{18}$ is $C_1$–$C_{24}$ alkyl, and, said 2-hydroxyphenylbenzotriazole represented by the structure,

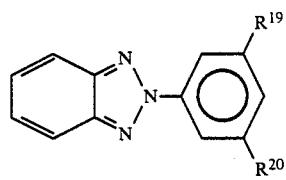

wherein $R^{19}$ is lower alkyl or halogen (preferably chlorine); $R^{20}$ is lower alkyl, halogen (preferably chlorine), or hydrogen; and, X is chlorine or hydrogen; the ratio of the 3,5-DHPZNA to the secondary stabilizer being in the range from about 5:1 to about 1:5.

11. The method of claim 10 for stabilizing a synthetic resinous material wherein said 3,5-DHPZNA is characterized by, n is 2 or 3, and Y is oxygen, O;

$R^1$ is $C_1$–$C_8$ alkyl, $R^2$ is $C_1$–$C_5$ alkyl, $R^3$ and $R^4$ are each $C_1$–$C_8$ alkyl, and together, when cyclized represent cyclohexyl, methylcyclohexyl, cycloheptyl;

$R^5$ is $C_1$–$C_8$ alkyl; and, $R^{10}$ is hydrogen or $C_1$–$C_8$ alkyl.

12. A process for preparing a N-(substituted)-1-(piperazinealkyl)-α-(3,5-dialkyl-4-hydroxyphenyl)-α,α-substituted acetamide, represented by the structure

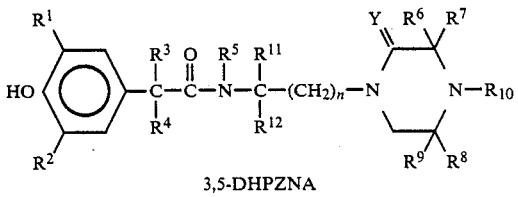

3,5-DHPZNA wherein, $R^1$, $R^2$ and $R^5$ each represnt hydrogen, $C_1$–$C_{12}$ alkyl, phenyl, naphthyl, $C_4$–$C_{12}$ cycloalkyl, and, alkyl-substituted cycloalkyl, phenyl and naphthyl, each alkyl substituent being $C_1$–$C_8$, and at least one of $R^1$ and $R^2$ is t-$C_4$–$C_{12}$ alkyl;

$R^3$ and $R^4$ independently represent $C_1$–$C_{18}$ alkyl, and $C_5$–$C_{12}$ cycloalkyl, phenyl and naphthyl, and, alkyl-substituted cycloalkyl, phenyl and naphthyl, each alkyl substituent being $C_1$–$C_8$, and, when together cyclized, $R^3$ with $R^4$ may represent $C_4$–$C_{12}$ cycloalkyl, and $C_1$–$C_8$ alkyl-substituted cycloalkyl;

$R^6$, $R^7$, $R^8$ and $R^9$ each represent $C_1$–$C_{12}$ alkyl, or, when together cyclized, $R^6$ with $R^7$, and $R^8$ with $R_9$, may represent $C_4$–$C_{12}$ cycloalkyl, and $C_1$–$C_8$ alkyl-substituted cycloalkyl;

$R^{10}$ is selected from the group consisting of hydrogen, $C_1$–$C_8$ alkyl and $$R^{13}-\overset{\overset{O}{\|}}{C}-$$

wherein $R^{13}$ represents hydrogen, $C_1$–$C_{18}$ alkyl or alkenyl, phenyl or naphthyl;

$R^{11}$ and $R^{12}$ independently represent hydrogen and $C_1$–$C_{18}$ alkyl;

n is an integer in the range from 1 to about 8; and,

Y represents $H_2$ when the diazacycloalkane ring is piperazinyl, and O when the diazacycloalkane ring represents piperazin-2-one;

said process comprising, reacting (i) a 2,6-dialkylphenol represented by the structure $$\underset{\text{(phenol with OH, } R^1, R^2)}{\text{structure}}$$

wherein, $R^1$ and $R^2$ have the same connotation as hereinabove, with (ii) an excess over stoichiometric of a ketone selected from the group consisting of $C_1$–$C_8$ dialkyl ketones, $C_5$–$C_8$ cycloalkanones, $C_1$–$C_8$ alkyl-cycloalkanes, and $C_1$–$C_8$ alkylphenyl ketones, and, (iii) a haloform selected from the group consisting of chloroform and bromoform, and, (iv) a 4-amino-polysubstituted piperazine represented by the structure $$\underset{H}{\overset{R^5}{N}}-\underset{R^{12}}{\overset{R^{11}}{C}}-(CH_2)_n-N\underset{R^9\ R^8}{\overset{Y\ R^6\ R^7}{\diagdown}}N-R_{10}$$

wherein

Y, $R^5$, $R^6$, $R^7$, $R^8$, $R^9$, $R^{10}$ $R^{11}$ and $R^{12}$ have the same connotation as that given hereinbefore, in the presence of an alkali metal hydroxide.

13. The process of claim 12 wherein said 3,5-DHPZNA is characterized by, n is 2 or 3, and Y is oxygen, O;

$R^1$ is $C_1$–$C_8$ alkyl, $R^2$ is $C_1$–$C_5$ alkyl, $R^3$ and $R^4$ are each $C_1$–$C_8$ alkyl, and together, when cyclized represent cyclohexyl, methylcyclohexyl, cycloheptyl;

$R^5$ is $C_1$–$C_8$ alkyl; and, $R^{10}$ is hydrogen or $C_1$–$C_8$ alkyl.

* * * * *